(12) United States Patent
Snell et al.

(10) Patent No.: US 10,420,591 B2
(45) Date of Patent: Sep. 24, 2019

(54) INTERSPINOUS IMPLANT INSERTION INSTRUMENT WITH STAGGERED PATH IMPLANT DEPLOYMENT MECHANISM

(71) Applicant: Spinal Simplicity, LLC, Overland Park, KS (US)

(72) Inventors: Douglas Snell, Overland Park, KS (US); Annaria Barnds, Roeland Park, KS (US); Adam Frock, Larwill, IN (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 15/487,087

(22) Filed: Apr. 13, 2017

(65) Prior Publication Data

US 2017/0296238 A1 Oct. 19, 2017

Related U.S. Application Data

(60) Provisional application No. 62/322,390, filed on Apr. 14, 2016.

(51) Int. Cl.
  *A61B 17/70* (2006.01)
  *A61F 2/46* (2006.01)
  *A61B 17/00* (2006.01)

(52) U.S. Cl.
  CPC ...... *A61B 17/7068* (2013.01); *A61B 17/7065* (2013.01); *A61B 17/7082* (2013.01);
  (Continued)

(58) Field of Classification Search
  CPC .................. A61B 17/7062–707; A61F 2/4611
  See application file for complete search history.

(56) References Cited

U.S. PATENT DOCUMENTS 6,299,616 B1 * 10/2001 Beger ................ A61B 17/7044
  606/86 A
9,757,250 B2 * 9/2017 Josse ..................... A61F 2/4611
(Continued)

FOREIGN PATENT DOCUMENTS

WO   WO-2015034943 A2   3/2015

OTHER PUBLICATIONS

International Search Report and Written Opinion of the International Searching Authority dated Oct. 16, 2017 in corresponding International Application No. PCT/US2017/027640.

*Primary Examiner* — Eduardo C Robert
*Assistant Examiner* — Michelle C Eckman
(74) *Attorney, Agent, or Firm* — Locke Lord LLP; Scott D. Wofsy

(57) ABSTRACT

An insertion instrument for inserting an implant includes an elongated main body having a proximal handle and a distal portion that selectively couples to the implant. A plunger is slidably engaged in a central passage of the elongated main body configured to fix the implant to the elongated main body by selectively filling the central passage within the distal portion. A hex nut driver is concentrically located about the plunger and elongated main body to deploy an actuation plunger of the implant. The proximal handle portion of the main body includes a staggered path therethrough for accepting a tab of the plunger therein. Advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant.

15 Claims, 14 Drawing Sheets

(52) U.S. Cl.
CPC ... *A61F 2/4611* (2013.01); *A61B 2017/00862* (2013.01); *A61F 2002/4615* (2013.01); *A61F 2002/4627* (2013.01); *A61F 2002/4635* (2013.01)

(56) References Cited

U.S. PATENT DOCUMENTS

| | | | |
|---|---|---|---|
| 9,855,058 B2* | 1/2018 | Morgenstern Lopez | A61B 17/1671 |
| 9,937,055 B1* | 4/2018 | Bernhardt, Jr. | H05K 999/99 |
| 9,987,146 B1* | 6/2018 | Lentner | A61F 2/447 |
| 2006/0149278 A1* | 7/2006 | Abdou | A61B 17/7065 606/90 |
| 2006/0155297 A1* | 7/2006 | Ainsworth | A61B 17/025 606/99 |
| 2008/0172060 A1* | 7/2008 | Collins | A61B 17/8811 606/94 |
| 2009/0012528 A1* | 1/2009 | Aschmann | A61B 17/7065 606/99 |
| 2009/0054988 A1* | 2/2009 | Hess | A61B 17/025 623/17.16 |
| 2009/0112220 A1* | 4/2009 | Kraus | A61F 2/44 606/99 |
| 2009/0198245 A1* | 8/2009 | Phan | A61B 17/7065 606/99 |
| 2009/0292316 A1* | 11/2009 | Hess | A61B 17/7065 606/249 |
| 2010/0234889 A1* | 9/2010 | Hess | A61B 17/7062 606/249 |
| 2011/0137358 A1 | 6/2011 | Manninen | |
| 2011/0230970 A1* | 9/2011 | Lynn | A61F 2/442 623/17.16 |
| 2012/0004729 A1* | 1/2012 | Zipnick | A61B 17/320016 623/17.16 |
| 2012/0078302 A1* | 3/2012 | Reimels | A61B 17/7065 606/249 |
| 2012/0088979 A1* | 4/2012 | Nunley | A61B 17/025 600/231 |
| 2012/0191135 A1* | 7/2012 | Abdou | A61B 17/7065 606/248 |
| 2012/0232601 A1* | 9/2012 | Chabansky | A61F 2/442 606/86 A |
| 2012/0271422 A1* | 10/2012 | Miller | A61F 2/447 623/17.16 |
| 2013/0006365 A1* | 1/2013 | Pepper | A61F 2/447 623/17.16 |
| 2014/0012318 A1* | 1/2014 | Goel | A61B 17/7064 606/247 |
| 2014/0100583 A1* | 4/2014 | Butler | A61B 17/7082 606/104 |
| 2014/0257194 A1 | 9/2014 | Edhouse et al. | |
| 2014/0358186 A1* | 12/2014 | Frock | A61B 17/8891 606/86 A |
| 2015/0032163 A1* | 1/2015 | Abdou | A61B 17/7065 606/279 |
| 2015/0045892 A1* | 2/2015 | Lynn | A61F 2/447 623/17.16 |
| 2015/0351925 A1* | 12/2015 | Emerick | A61F 2/447 623/17.16 |
| 2016/0008140 A1 | 1/2016 | Melkent et al. | |
| 2016/0030195 A1* | 2/2016 | Prevost | A61F 2/4611 623/17.16 |
| 2016/0058575 A1* | 3/2016 | Sutterlin, III | A61F 2/4465 623/17.16 |
| 2016/0128847 A1* | 5/2016 | Kurtaliaj | A61F 2/4611 623/17.16 |
| 2016/0262805 A1* | 9/2016 | Rogers | A61B 17/7068 |
| 2016/0296344 A1* | 10/2016 | Greenhalgh | A61F 2/4601 |
| 2017/0056201 A1* | 3/2017 | Liang | A61F 2/4455 |
| 2017/0151065 A1* | 6/2017 | Warren | A61F 2/4611 |
| 2017/0151068 A1* | 6/2017 | Morgenstern Lopez | A61B 17/1757 |
| 2017/0189204 A1* | 7/2017 | Riemhofer | A61F 2/4611 |
| 2017/0209284 A1* | 7/2017 | Overes | A61F 2/4455 |
| 2017/0216045 A1* | 8/2017 | Dewey | A61F 2/447 |
| 2017/0266015 A1* | 9/2017 | Overes | A61B 17/8615 |
| 2017/0290678 A1* | 10/2017 | Olmos | A61F 2/4611 |
| 2017/0296238 A1* | 10/2017 | Snell | A61B 17/7065 |
| 2017/0312092 A1* | 11/2017 | Link | A61F 2/4455 |
| 2017/0333219 A1* | 11/2017 | Josse | A61F 2/4611 |
| 2018/0014944 A1* | 1/2018 | Davis | A61F 2/447 |
| 2018/0028333 A1* | 2/2018 | Willis | A61F 2/44 |
| 2018/0064558 A1* | 3/2018 | Puno | A61B 17/1757 |
| 2018/0110629 A1* | 4/2018 | Ewer | A61F 2/4455 |
| 2018/0116815 A1* | 5/2018 | Kuyler | A61F 2/447 |
| 2018/0161077 A1* | 6/2018 | McCormack | A61B 17/025 |
| 2018/0161175 A1* | 6/2018 | Frasier | A61F 2/4611 |

\* cited by examiner

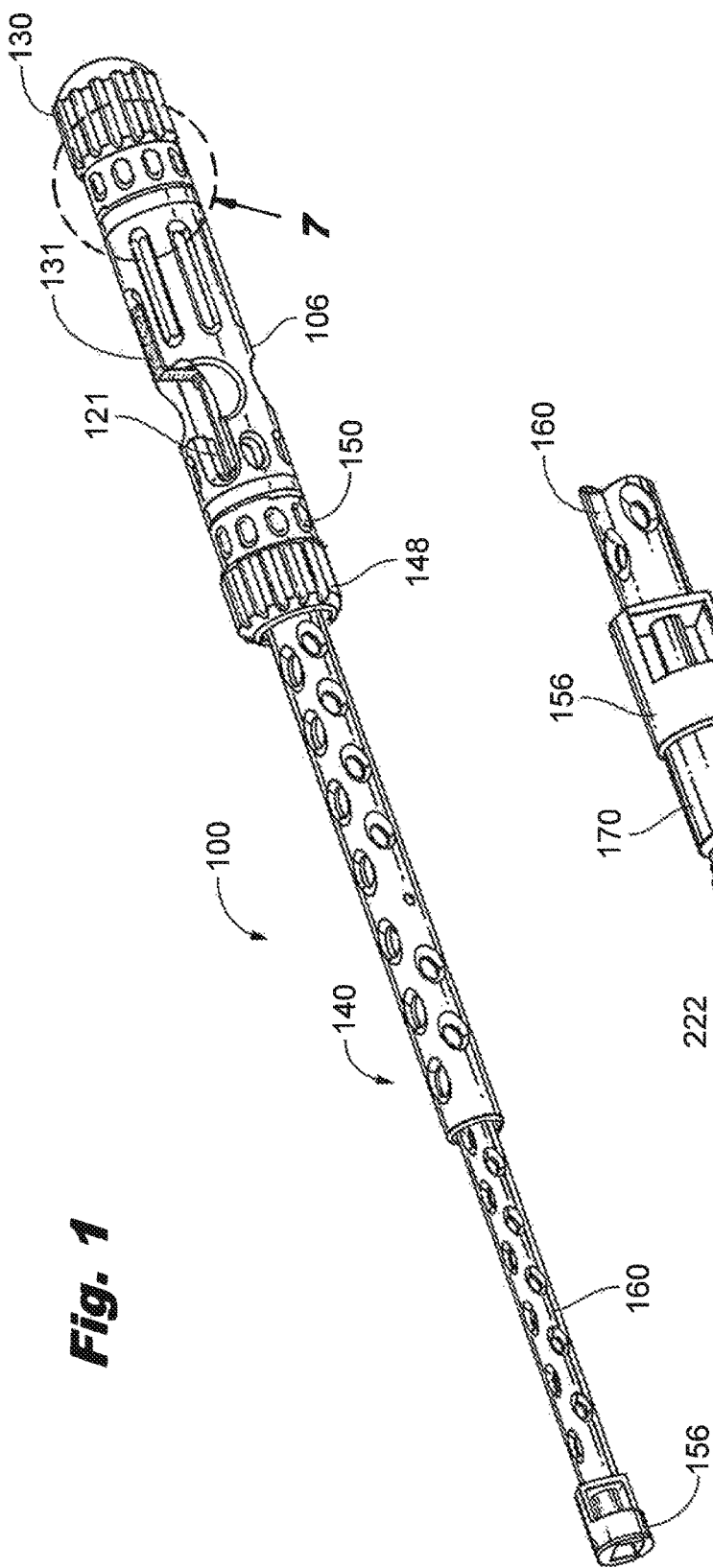

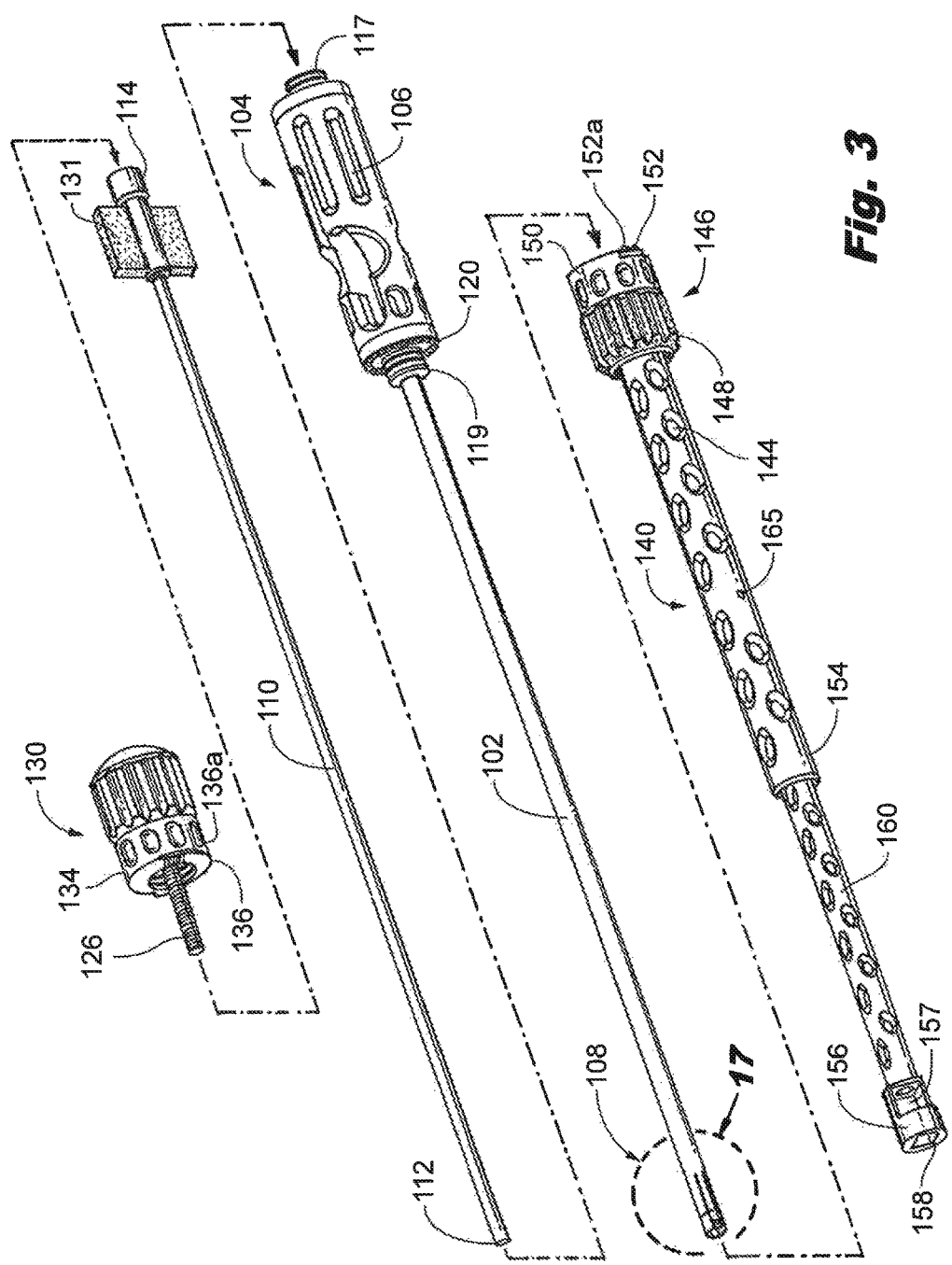

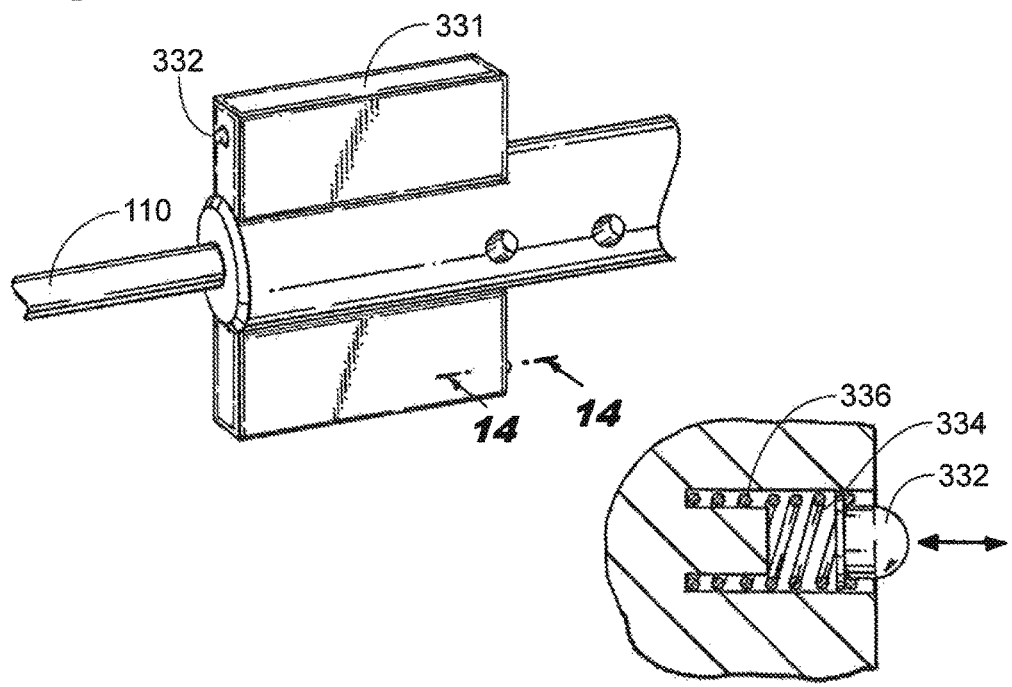
Fig. 13
Fig. 14
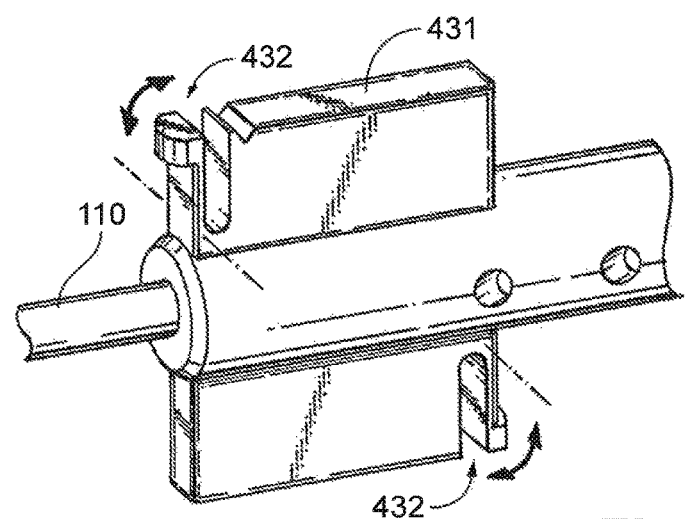
Fig. 15 ic # INTERSPINOUS IMPLANT INSERTION INSTRUMENT WITH STAGGERED PATH IMPLANT DEPLOYMENT MECHANISM

CROSS-REFERENCE TO RELATED APPLICATIONS

This application claims the benefit of and priority to U.S. Patent Application Ser. No. 62/322,390, filed Apr. 14, 2017, which is incorporated herein by reference in its entirety. The interspinous implant insertion instrument of the subject invention relates to the insertion instrument disclosed in commonly assigned U.S. Patent Application Publication 2014/0358186, the disclosure of which is incorporated herein by reference in its entirety.

BACKGROUND OF THE INVENTION

1. Field of the Invention

The subject technology is directed to instruments for inserting spinal implants, and more particularly, to an insertion instrument that is easily assembled and disassembled for required cleaning while being able to effectively deploy an interspinous process implant for spinal stabilization, for percutaneous placement in a target interspinous process space, wherein the implant can also serve as a fusion cage spacer to treat lumbar spinal stenosis.

2. Description of Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. Some surgical procedures for treating spinal stenosis are decompressive laminectomy and interspinous process decompression (IPD). A well-known implant used for performing IPD surgery is the X-STOP® device, which is described in U.S. Pat. No. 6,419,676, the disclosure of which is herein incorporated by reference in its entirety. Another interspinous process implant placed in a minimally invasive surgical procedure is disclosed in U.S. Patent Application Publication 2008/0243250, which is also incorporated herein by reference in its entirety.

Still another interspinous process implant placed in a minimally invasive surgical procedure is disclosed in U.S. Patent Application Publication 2010/0234889, which is also incorporated herein by reference in its entirety. One aspect of effective insertion of these implants is to provide a low profile instrument for deploying the implant. Often, the insertion instrument has several moving parts. Because of the cost of the insertion instruments, the instruments are re-used many times. For such insertion instruments to be re-used, the insertion instruments must be properly and fully cleaned without damage or loss of the components.

SUMMARY OF THE INVENTION

An insertion instrument for inserting an implant includes an elongated main body having a proximal handle and a distal portion that selectively couples to the implant. A plunger is slidably engaged in a central passage of the elongated main body configured to fix the implant to the elongated main body by selectively filling the central passage within the distal portion. A hex nut driver is concentrically located about the plunger and elongated main body to deploy an actuation plunger of the implant. The proximal handle portion of the main body includes a staggered path therethrough for accepting a tab of the plunger therein. Advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant.

The insertion instrument includes a plunger knob rotatably coupled to the plunger wherein rotation of the knob translates the plunger tab within the staggered path. The staggered being a cut-out in the proximal handle that includes two parallel linear paths with a perpendicular transition wall therebetween. Rotation of a plunger knob translates the plunger tab proximally and distally and wherein rotation of the handle transitions the plunger tab along the transition wall and between the two linear paths.

The insertion instrument further includes a knob of the hex nut driver which can be rotatably coupled to a distal threaded portion of the handle through a distal end cap wherein the knob of the hex nut is configured to deploy the implant. The insertion instrument may further include a plunger knob rotatably coupled to a proximal threaded portion of the handle through a proximal end cap wherein the plunger knob is configured to translate the plunger tab within the staggered path.

In an embodiment, the plunger tab, a plunger knob, and a knob of the hex nut driver include a black PVD coating configured to indicate portions of the insertion instrument that change position during operation.

The insertion instrument may still further include a proximal end cap between a plunger knob and a proximal portion of the handle and a distal end cap between a distal portion of the handle and a knob of the hex nut driver. The proximal end cap can include at least one flexible tooth corresponding to a plurality of ratchet teeth of the handle. The at least one flexible tooth and plurality of ratchet teeth configured to auto-lock the plunger and plunger knob to the handle and prevent premature loosening. The distal end cap can include at least one flexible tooth corresponding to a plurality of ratchet teeth of the handle. The at least one flexible tooth and plurality of ratchet teeth configured to auto-lock the hex nut driver and the handle together and prevent premature loosening.

The distal portion of the main body can include at least two flexible arms configured to friction fit the implant to the insertion instrument. A tip of the distal portion of the main body can match an inner diameter of the implant thereby configured to control mounting, torqueing and retention of the implant with the main body.

In the unlocked position, the plunger tab is in the proximal most position of the staggered path. In the locked position, the plunger tab is positioned adjacent a transition wall of the staggered path. In the deployed position, the plunger tab is in the distal most position of the staggered path.

In one embodiment, the plunger tab is positioned at a proximal portion of the plunger and is generally rectangular with the plunger extending through a central portion thereof. In another embodiment, the plunger tab includes at least two ball nose springs disposed on opposing faces of the plunger tab. In yet another embodiment, the plunger tab includes flexible tabs disposed on opposing faces of the plunger tab.

An insertion device for a spinal implant, wherein the spinal implant includes an elongated body to function as a spacer placed in a target interspinous process space between two adjacent spinous processes. The body defines an interior and a proximal internal recess for access to the interior, the proximal internal recess forming a transverse groove. A distal anchor that is at least partially threaded and has opposing radially deployable blades is mounted for rotation about a pin transversely mounted in the interior. A proximal anchor including a spike cap is mounted to slide along the body and a drive nut mounted for longitudinal movement along the body between a first position spaced apart from the distal anchor and a second position relatively closer to the distal anchor to thereby compress the two adjacent spinous processes between the spike cap and the distal anchor. An actuation plunger is slidably inside the interior for moving the blades from a stowed position to an implant deployed position.

The insertion device includes an elongated main body having a distal locking portion for coupling to the implant and a proximal handle portion. The main body defining a central passage and the distal locking portion having at least one flexible arm to flex radially inward. A plunger is slidably coupled in the central passage for movement between an unlocked position for mounting the implant on the distal locking portion, a locked position for locking the implant on the distal locking portion, and an insertion instrument deployed position for deploying the actuation plunger to move the blades from the stowed position to the deployed position. A hex nut driver rotatably mounted on the main body having a socket end for engaging the drive nut to, in turn, move the hex nut. The proximal handle portion of the main body includes a staggered path therethrough for accepting a tab of the plunger therein configured to control the advancement and retraction of the plunger within the central passage of the main body.

In the unlocked position, when the implant is mounted on the insertion instrument, the plunger tab is in the proximal most position of the staggered path and the flexible arms are in the transverse groove. In the locked position, the plunger tab is positioned adjacent a transition wall of the staggered path, the flexible arms are in the transverse groove and the plunger extends through the central passage to be concentric with the flexible arms. In the deployed position, the plunger tab is in the distal most position of the staggered path, the plunger extends out of the central passage to move the actuation plunger of the implant.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those skilled in the art to which the subject invention relates will readily understand how to make and use the insertion instrument of the subject technology without undue experimentation, embodiments thereof will be described in detail herein below with reference to the following figures.

FIG. 1 is a perspective view of an insertion instrument in accordance with a first exemplary embodiment of the subject technology.

FIG. 2 is a perspective view of a distal portion of the insertion instrument of FIG. 1 with an implant in accordance with a first exemplary embodiment of the subject technology.

FIG. 3 is an exploded view of the insertion instrument of FIG. 1, illustrating the components thereof.

FIG. 13 is a perspective view of an alternate embodiment of a plunger tab, showing a spring-loaded detent.

FIG. 14 is a cross-section view taken along line 14-14 of FIG. 13, showing an internal spring.

FIG. 15 is a perspective of another alternate embodiment of a plunger tab, showing integrated flexible legs.

DETAILED DESCRIPTION

Figure 4:
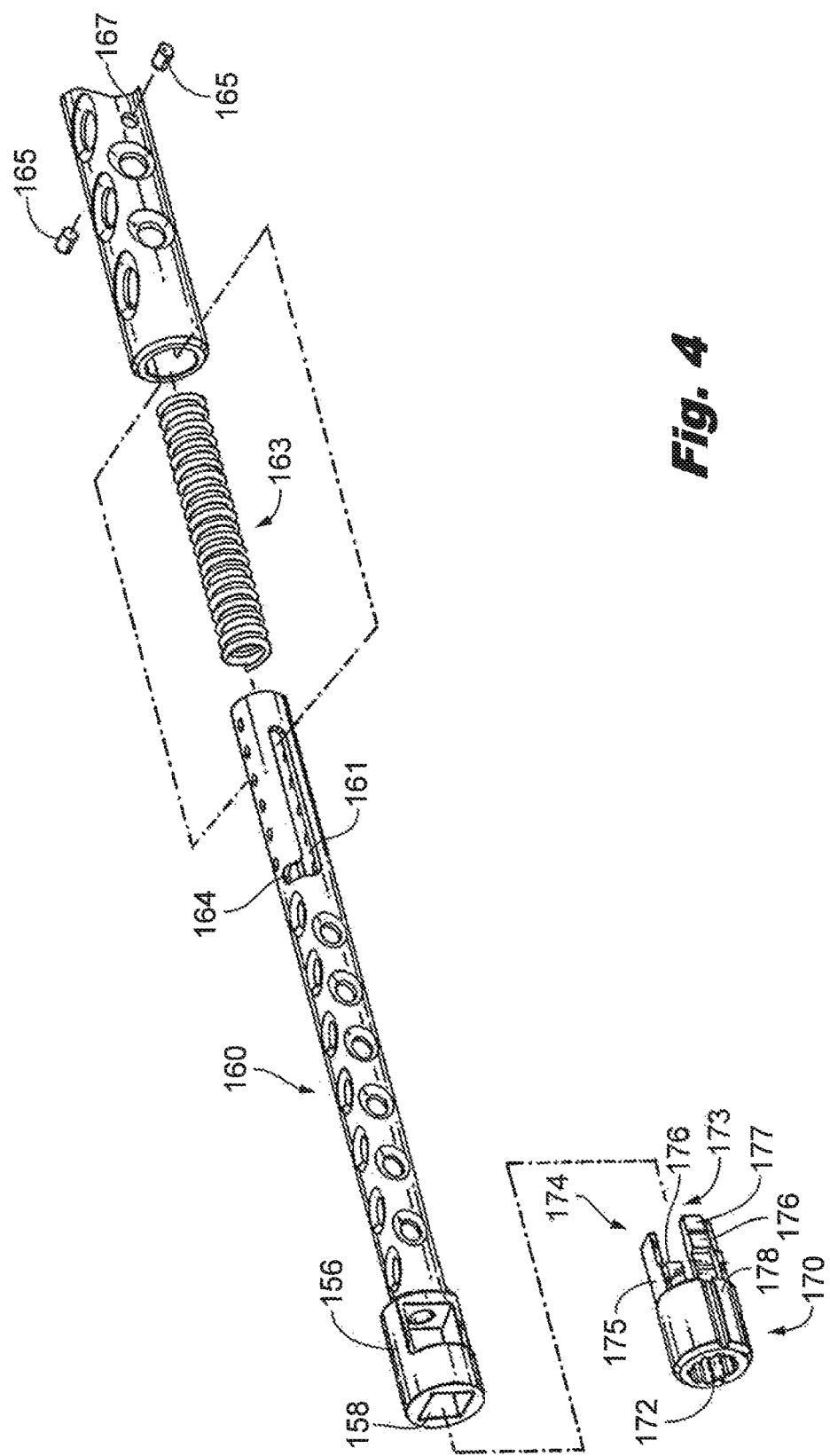
FIG. 4 is an exploded view of a hex nut driver and adapter for coupling to the implant.

The present disclosure overcomes many of the prior art problems associated with instruments for inserting spinal implants and other devices such as cage spacers and the like. The advantages and other features of the instruments and methods disclosed herein will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as left, right, up, and down are with reference to the Figures, and not meant in a limiting sense. The illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed systems or methods. The shapes and sizes of components are also exemplary and unless otherwise specified, can be altered without materially affecting or limiting the disclosed technology.

Insertion Instrument

Referring now to FIG. 1, a perspective view of an assembled instrument 100 for inserting an implant in accordance with the subject technology is shown. The instrument 100 is particularly useful for inserting interspinous process implants and fusion cage spacers in accordance with those shown in U.S. PG Pub. No. 2010/0234889 (the '889 application).

Referring additionally to FIG. 2, a perspective view of a distal portion of the insertion instrument 100 mounted with an implant 200 in accordance with the '889 application is shown. The insertion instrument includes four sub-assemblies that work together to lock and deploy an implant into an interspinous space. As best seen in FIG. 3, the four sub-assemblies include: an elongated main body 102 with a handle 106 at a proximal portion, a plunger knob 130, a plunger 110 which couples to the plunger knob 130 and handle 106, and a hex nut driver 140 concentrically about the plunger 110.

After use, the instrument 100 can be disassembled easily to allow for full and proper cleaning, then reassembled to be used again. Preferably, the components of the instrument 100 are fabricated from medical grade stainless steel, alloys, and/or polymers (e.g., RULON, PEEK) or another like durable material to allow for repeated use, cleaning and reuse.

Figure 17:
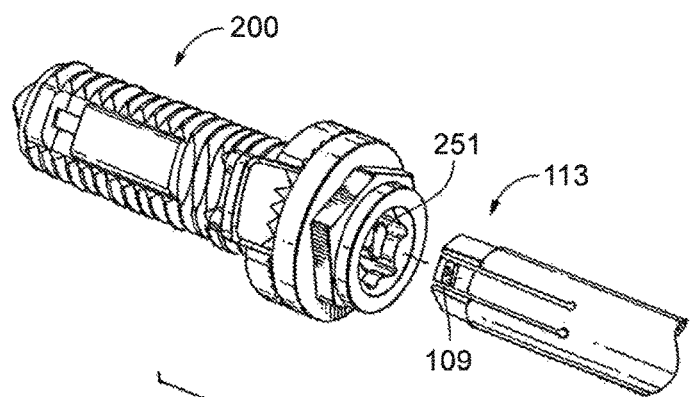
FIG. 17 is a perspective view of an implant and a distal portion of the main body, showing a hex-shaped shaft and football-shaped detents.

With continued reference to FIG. 3, the elongated main body 102 defines a central passage 106 and a distal portion 108 that selectively couples to the implant 200. The distal portion 108 includes flexible arms 109 (shown in FIG. 17) that allow compression of the tip 113. The tip 113 is roughly hexagonal shaped but with flexible arms 109. The tip 113 includes a generally "football shaped" detent feature 109a which controls the mounting, torqueing and retention of an implant.

The handle 104 of the main body 102 includes a proximal threaded feature 117 and a distal threaded feature 119 on a respective proximal face and distal face. The proximal threaded feature 117 couples the handle 106 to the plunger knob 130 and the distal threaded feature 119 couples the handle 106 to a knob 148 of the hex nut driver 140.

The plunger 110 slides into the central passage 106 of the elongated main body 102. The plunger 110 has a distal pushing end 112 for engaging the implant 200 and a proximal locking end 114. The proximal locking end 114 rotatably couples the plunger 110 to the plunger knob 130 and has a relatively thicker radius than the distal pushing end 112. Abutting the proximal locking end 114 is a plunger tab 131 extending outwardly. The plunger tab 131 is substantially rectangular with the plunger 110 extending through a central portion thereof.

The handle 106 includes a staggered path 121 (best seen in FIG. 9) for accepting the plunger tab 131 therein. More specifically, the staggered path 121 is a cut-out in the handle 106 that includes two parallel linear paths 123, 125 with a perpendicular transition wall 127 therebetween. As will be discussed in further detail throughout the disclosure, rotational movement of the plunger knob 130 moves the plunger tab 131 proximally and distally within the staggered path 121 allowing the plunger 110 to act as its own advancement and retraction mechanism.

Figure 16:
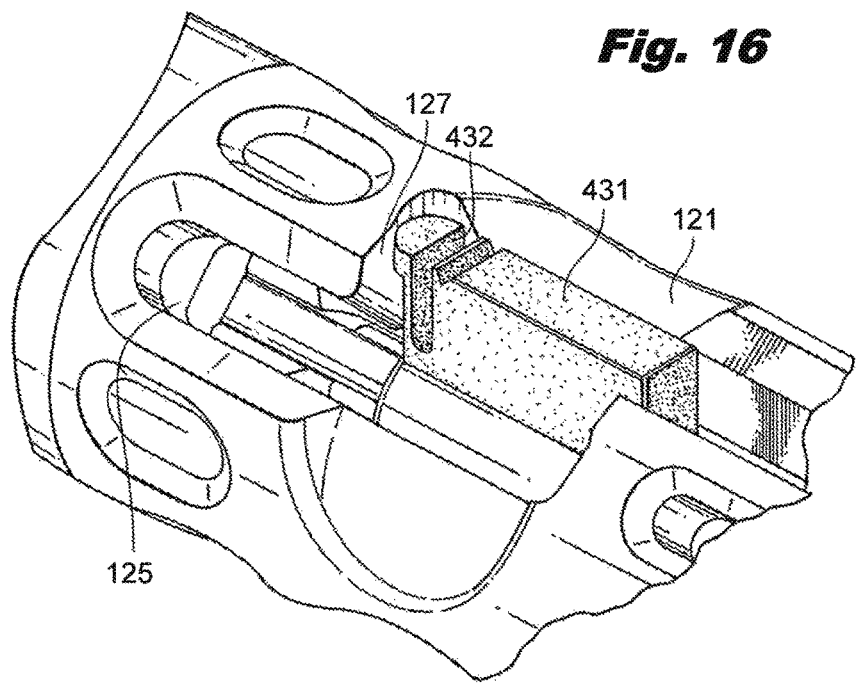
FIG. 16 is a perspective of the with the plunger tab of FIG. 15, showing tabs secured with the transition wall.

FIGS. 13-16 illustrate additional embodiments of the plunger tab. In FIGS. 13 and 14, the plunger tab 331 includes a ball nose spring 332 and 334 on a proximal face and a distal face. The spring is positioned within a recess 336. FIGS. 15 and 16, integrated flexible tabs 432 are included in plunger tab 431. The flexible tabs 432 are also positioned along a proximal and distal face of the plunger tab 432. The ball nose spring 332 and the flexible tabs 432 engage the staggered path 121 and prevent accidental rotation of the plunger 110.

The hex nut driver 140 defines an axial passage 144 for receiving the distal end 108 of the main body 102. The hex nut driver 140 has a proximal portion 146 that includes a relatively larger radius handle portion 148 with end cap 150. A tubular intermediate portion 154 extends from the handle portion 148 and slidingly receives a drive shaft 160. The drive shaft 160 terminates in a socket end 156. The socket end 156 is also tubular but forms a square opening 158 for coupling to the implant 200. The socket end 156 also forms a transverse square locking passage 157.

The drive shaft 160 can be locked in a retracted position within the intermediate portion 154. Referring now to FIG. 4, an exploded view of the hex nut driver 140 is shown. The hex nut driver 140 has a spring 163 mounted within the intermediate portion 154 for biasing the drive shaft 160 distally. In order to lock the drive shaft 160 in a retracted position, the bias of the spring 163 must be overcome. To accomplish this locking, the drive shaft 160 forms two opposing complimentary slots 161 (only one slot 161 can be seen) and pins 165 mounted in opposing pinholes 167 on the intermediate portion 154. When assembled, the pins 165 ride in the respective slots 161 so that upon fully pushing the drive shaft 160 in the intermediate portion 154, a small rotation of the drive shaft 160 will set the pins 165 in a radial portion 164 of the slots 161 and retain the hex nut driver 140 in this compressed position.

An adapter 170 attaches to the square opening 158 of the hex nut driver 140 to provide a hex socket 172 for coupling to the implant 200. The hex socket 172 can vary in size to accommodate different size implants 200. The adapter 170 has a central axial passage 173 to slide over the tip 113 of the main body 102. The adapter 170 has a standard male square open proximal end 174 to couple to the square opening 158. The proximal end 174 has two opposing rigid legs 175 intermediate two opposing flexible legs 176. Each of the flexible legs 176 has a locking tab 177 so that as the proximal end 174 is pushed into the square opening 158 of the hex nut driver 140, the legs 176 deflect to allow easy insertion, then the tabs 177 couple to the transverse locking passage 157 to securely retain the adapter 170 on the drive shaft 160. To remove the adapter 170, the locking tabs 177 are simply depressed while retracting the adapter 170. The adapter 170 also has opposing outer axial alignment ridges 178.

The Implant

The implant 200 may take a variety of different configurations and sizes. Preferably, the implant is useful for treatment of spondylolisthesis, central and foraminal lumbar stenosis, degenerative disc disease and the like. Beneficially, the implant 200 is percutaneously placed, provides stabilization of the spine, can be used with bone graft material to promote fusion, requires less than a 2.6 cm incision, and can be inserted with local or general anesthesia. As such, the recovery time is relatively quicker and the hospital stay is relatively shorter. The implant is shown and described with partial features shown and described for the sake of brevity. Further details can be found in the '889 application and in U.S. Patent Application Publication 2014/0358186 both of which are incorporated by reference herein in their entirety.

Figure 18:
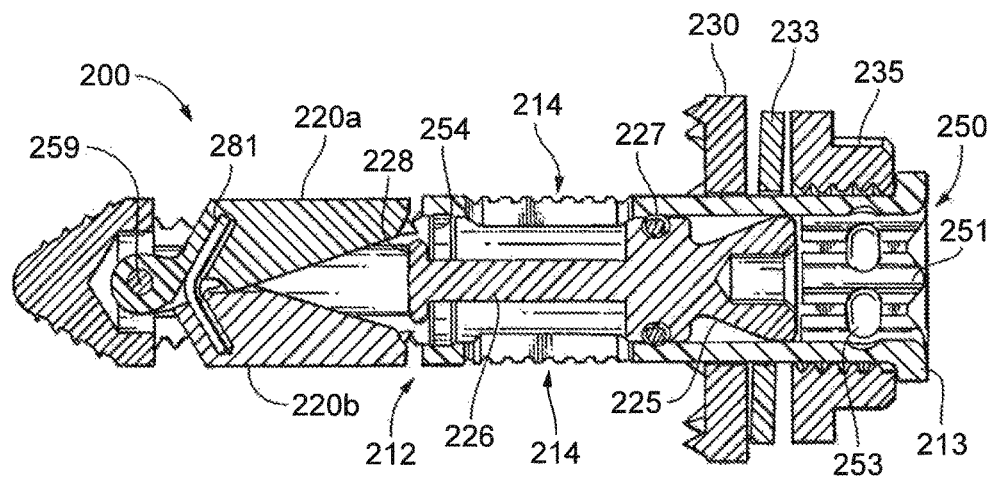
FIG. 18 is a cross-sectional view of the implant, showing the distal anchor elements are in a stowed position.
Figure 19:
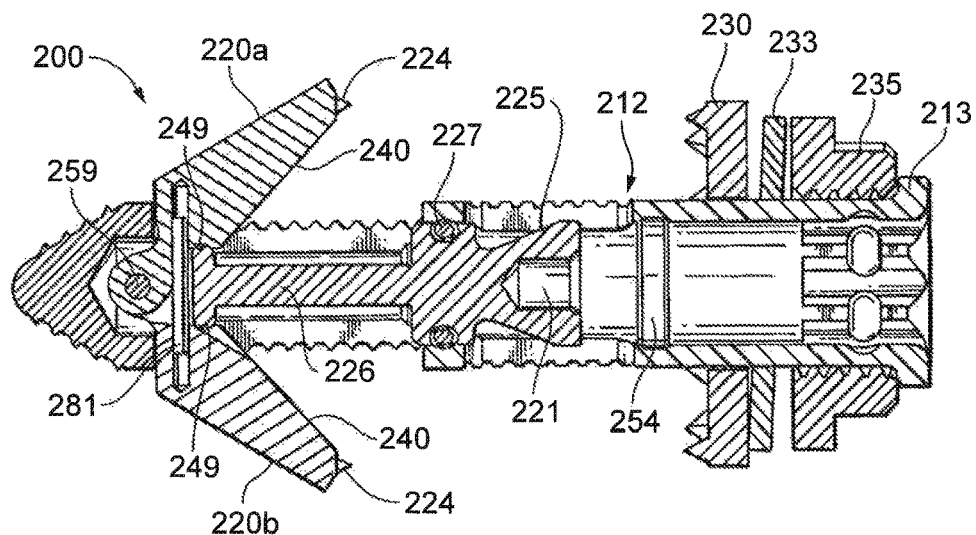
FIG. 19 is a cross-sectional view of the implant, showing the distal anchor elements in a deployed position.

FIGS. 18 and 19 illustrate in detail the interspinous process implant 200 for use the with insertion instrument 100. The implant 200 includes a body 212, providing overall structure to the implant 200. The body 212, as illustrated, is provided with threads 222 (shown in FIG. 1) for facilitating insertion of the implant 200 into a target interspinous process space 382 (FIGS. 20-21) as will be described in more detail below, as well as for providing additional engagement with the anatomy of the patient in the target interspinous process space 382. Further, the threads 222 permit rotational engagement between the body 212 and a proximal nut 235, provided to securely engage the implant 200 with interspinous processes 381a, 381b adjacent the target interspinous process space 382, which will be described in more detail below. Alternatively, the implant 200 can be provided without threads thereon, or with threads provided only on a portion thereof for one of the foregoing functions. That is, if desired, threads 222 can be provided only on the proximal end of the body 212, for engaging the nut 235 and not on the distal portion, or vice versa.

The implant 200 includes a distal anchor portion, which is configured as two opposed deployable blades 220 (220a, 220b). The blades 220 are provided with a common pivot, defined by a pin 259 passing therethrough, as well as through the body 212. Use of a common pivot advantageously minimizes the space required for housing all elements within the body 212 in their stowed state, although variations from this precise configuration are possible. For example, two separate pivots can be provided for each blade 220a, 220b, still in keeping with the invention. The blades 220, as illustrated, are provided with proximally directed spikes 224 for engaging the relevant adjacent bony anatomy, such as the spinous processes 381a, 381b. The blades 220 can alternatively be provided without such spikes 224.

In the illustrated embodiment, an implant plunger 226 is provided and includes a head portion 228 shaped and configured to act as a cam and cooperate with inner cam surfaces 240 formed on each of the blades 220a, 220b, as described above. As the plunger head 228 moves distally, cam surfaces 240 of the blades 220a, 220b follow the outer surface of the plunger head 228, and urge the blades 220a, 220b radially outwardly. In addition, the plunger 226 can include, as described above, a proximal head 225 having a proximal internal recess 221, and an angled distal surface to facilitate distally-directed urging and proximal-directed urging, respectively, applied from the proximal direction.

Preferably, the implant plunger 226 also includes a resilient catch 227. The catch 227 is configured to interface between the implant plunger 226 and internal surface features of the body 212, such as annular grooves or recesses 254. As described, the resilient catch 227 permits axial movement of the implant plunger 226, and in conjunction with the above-described internal surface features of the body 212, defined positions at which the implant plunger 226 is held, inhibiting unintentional movement therefrom. The catch 227 can be formed of any suitable material or configuration, such as from a resilient material, such as an elastomer, or as a resilient structure, such as a toroidal metallic coil, or a combination of these, for example. The catch 227 can be, in accordance with the invention, a canted coil, such as a Bal Latch™, available from Bal Seal Engineering, Inc. of Foothill Ranch, Calif., USA.

When deployed, as shown in FIG. 19, the blades 220 function in concert with the spike cap 230, which is axially moveable along the length of the implant 200. The nut 235 includes threads on its inner surface that engage the threads 222 provided on the outer surface of the body 212. Accordingly, rotational movement of the nut 235 yields axial movement thereof. When that axial movement is in the distal direction, the nut 235 urges the spike cap 230 distally until the spike cap 230 abuts the bony structures (e.g. spinous processes 381a, 381b) surrounding the target interspinous process space 382. If provided, protrusions or spikes 234 on the proximal anchor portion facilitate engagement with the bone and thus stabilization of the entire vertebrae-implant construct.

With continued reference to the cross-sectional views of FIGS. 18 and 19, the blades 220 can be provided with an internal spring element 281, spanning between respective recess in each of the blades 220a, 220b. The spring element 281 can be provided straight to maintain the blades 220a, 220b deployed (open) normally, or alternatively, bent, to maintain the blades 220a, 220b stowed (contracted) normally. In accordance with one aspect, the spring element 281 is provided bent, and urges the blades 220a, 220b inwardly, toward the stowed position, prior to and during implantation. Thus, in connection with the implant plunger 226, the spring 281 serves to maintain a position of the blades 220. As illustrated, when the implant plunger 226 is fully extended, a head portion 228 thereof engages a corresponding detent 249 in the blades 220a, 220b. The engagement of the detent 249 by the head portion 228 further ensures secure deployment of the blades 220a, 220b.

The spring element 281 can alternatively be provided as normally straight, urging the blades 220a, 220b outwardly toward the deployed position, prior to, during and following implantation. During implantation, however, the spring element 281 permits inward rotation of the blades 220a, 220b, temporarily bending the spring element 281 in the process. Thus, during implantation the spring 281 serves to maintain a position of the blades 220a, 220b against externally applied forces. Once placed in the target interspinous process space 382, the implant plunger 226 can be urged distally in order to lock the blades 220a, 220b in the deployed position. Engagement of the detent 249 by the head portion 228 of the implant plunger 226 further ensures maintenance of that position.

The body 212 of the implant 200 includes at its proximal end, an expanded-diameter portion 213, defining a proximal-most limit for traveling of the nut 235, spike cap 230 and a lock washer 233. Also in the proximal end portion, formed within the proximal internal recess 250, is a shaped socket 251 for engagement with the insertion instrument 100. As illustrated, the socket 251 is substantially hexagonal, with flat portions defined at regular angular intervals. Practicable departures from the precise configuration illustrated are possible. The shaped socket 251 facilitates mutual rotational engagement between the implant 200 and the insertion instrument 100.

Also provided in connection with the socket 251, are transverse grooves 253, which, in conjunction with the tip 113 of the main body 102 and pushing end 112 of the plunger 110 mount and lock the implant 100 to the insertion instrument 100. The mounting and/or locking elements on the insertion instrument can also be, for example, a resiliently and optionally lockable protrusion extending laterally (i.e., radially) from the insertion instrument. The lockable protrusion may be, for example, a lockable spring-loaded spherical element, for example.

The implant 200 can be provided with one or more apertures 214 to permit packing of the implant, such as in the proximal internal recess 250 thereof, with osteogenesis-promoting substances to facilitate bone ingrowth and/or fusion, such as demineralized bone.

Assembly of the Insertion Instrument

Referring now to FIGS. 3-8, the insertion instrument is designed for ease of assembly. The distal portion 108 of the main body 102 is inserted into the axial passage 144 of the hex nut driver 140. The knob 148 of the next nut driver 140 is rotated to couple the distal threading 119 of the handle 106 with the end cap 150 of the hex nut driver 140.

Figure 5:
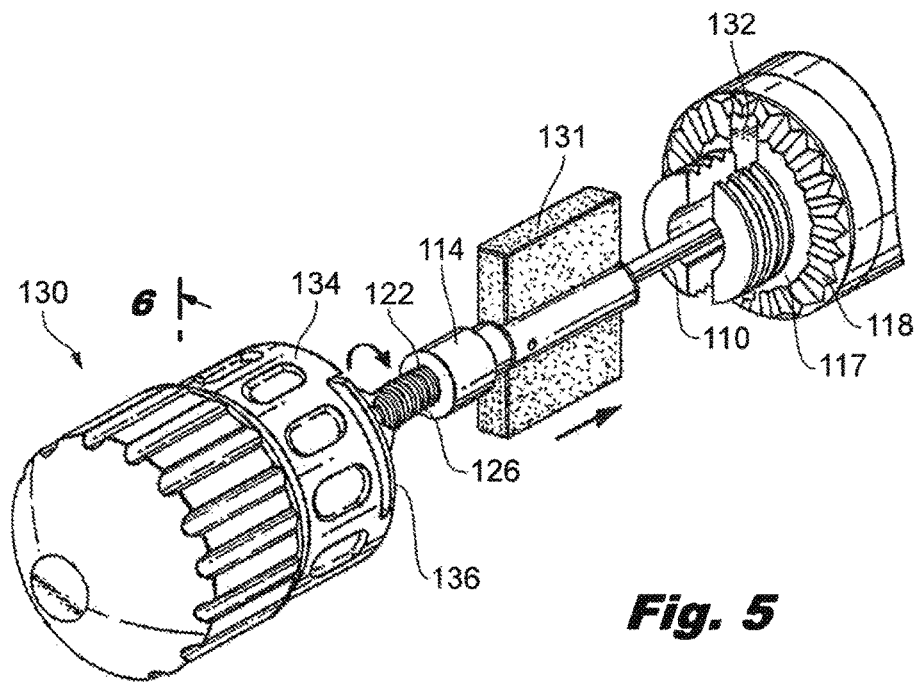
FIG. 5 is an exploded view of a plunger knob and plunger of the insertion instrument of FIG. 1, illustrating the components thereof.
Figure 6:
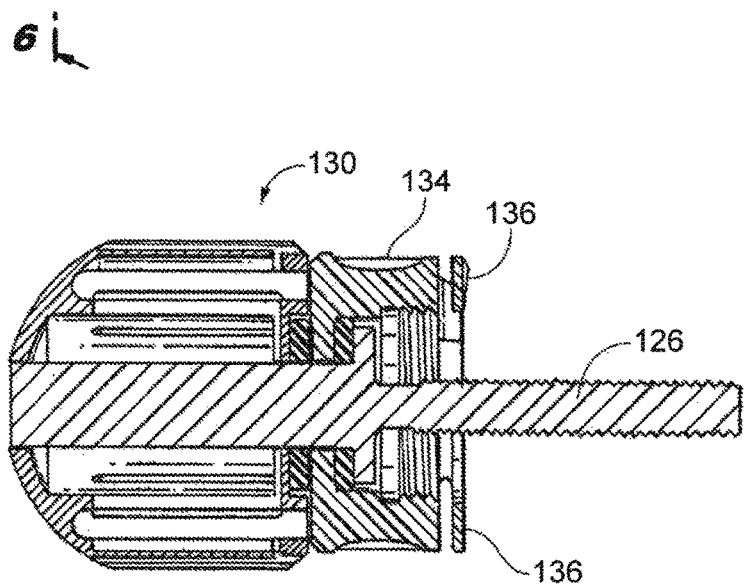
FIG. 6 is a side sectional view of the plunger knob of FIG. 5.

As best shown in FIG. 5, the plunger knob 130 is next coupled to the locking cap 114 of the plunger 110. The plunger knob 130 includes a threaded core 126 that is rotated into a recess 122 of the locking cap 114. The plunger 130 can next be inserted into the main body 102. The handle 132 includes an opening 132 for slideably engaging the plunger tab 131 therein. As the plunger 110 and plunger tab 131 are slid within the handle 106, the end cap 134 of plunger knob 130 abuts the proximal face of the housing 106. The plunger knob 130 is rotated to threadably engage the proximal threaded feature 117 of the handle 106 and secure the plunger 110 and plunger knob 130 to the handle 106.

Figure 7:
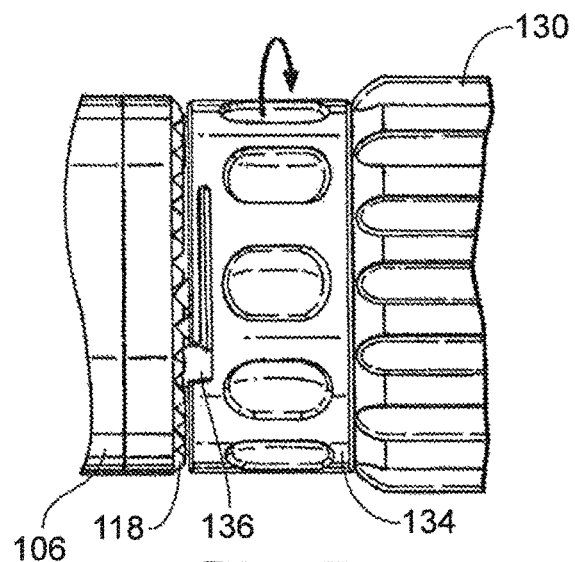
FIG. 7 is a side elevation view of the plunger knob and end cap, showing an auto-lock feature in closed position.
Figure 8:
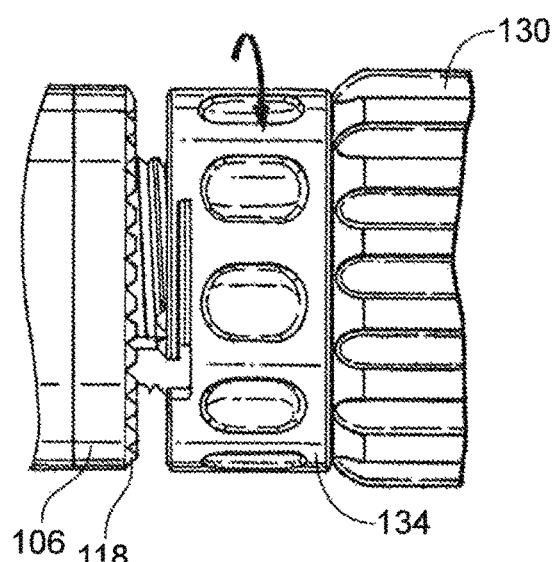
FIG. 8 is a side elevation view of the plunger knob and end cap, showing an auto-lock feature in an open position.

With reference to FIGS. 7 and 8, the insertion instrument 100 includes an auto-lock feature which enables a secure surgical instrument assembly while also allowing for disassembly without the use of additional tools. Each of the proximal face and distal face of the handle 106 include a plurality of ratchet teeth 118, 120, respectively. The plunger knob 130 and the knob 148 of the hex nut driver 140 each include an end cap 134, 150 welded thereto, respectively, that includes a flexible tab 136, 152 with at least two teeth 152*a* (shown best on end cap 152). As the plunger knob 130 and corresponding end cap 134 are threaded clockwise to the handle 106, the teeth 136*a* of the flexible tabs 136 engage with the ratchet teeth 118 of the proximal face and lock the handle 106 with the plunger knob 130. Similarly, as the hex nut driver 140 and corresponding end cap 150 are threaded clockwise to the handle 106, the teeth 152*a* of the flexible tab 152 engage with the ratchet teeth 120 of the distal face and lock the handle 106 and the hex nut driver 140. As shown in FIG. 8, counterclockwise motion loosens the teeth 136*a*, 1152*a* of each of the flexible tabs 134, 152 on the respective end caps 134, 150 and thereby allows for disassembly.

Figure 9:
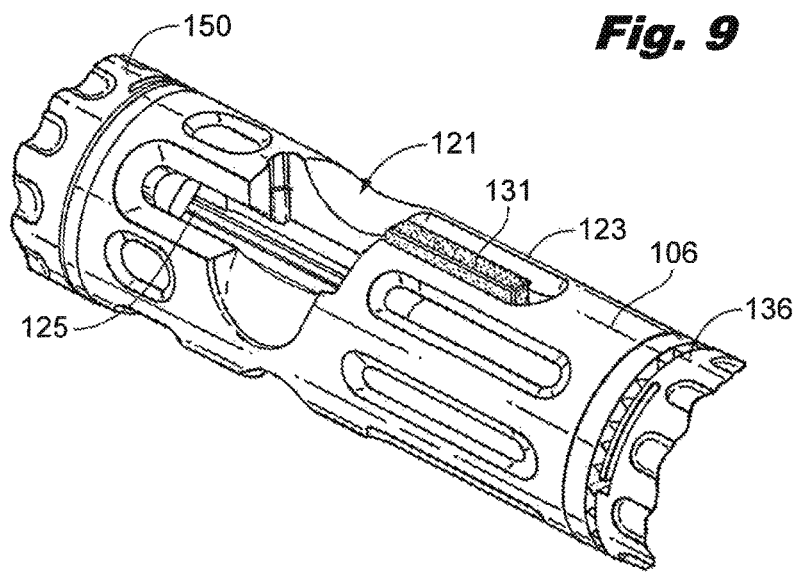
FIG. 9 is a perspective view of a handle of the insertion instrument of FIG. 1 with the plunger tab in a proximal position.

At this point, with the plunger 110 and plunger knob 130 secured to the handle 106, the plunger tab 131 is in the proximal position within the staggered path 121 (as shown in FIG. 9). The instrument 100 is now in the "unlocked" position. "Unlocked" refers to the implant 200 not being secured to the insertion instrument 100 even if the implant 200 is mounted on the tip 113.

The implant 200 is locked to the insertion instrument 100 by deploying the plunger 110 as described below.

Locking the Implant to the Insertion Instrument

To lock the implant 200 to the insertion instrument 100 the plunger 110 should be fully retracted into the unlocked position. This can be easily viewed by the plunger tab 131 being in the proximal most location within the staggered path 121 of the handle 106.

During use three components of the insertion instrument are used to translate the plunger 110 and deploy the implant 200: the plunger knob 130, the plunger tab 131 and the knob 148 of the hex nut driver 140. Each of these components includes a coating with PVD. The black PVD coating provides anti-galling coating as well as a usability indicator to the user as to which instrument components are manipulated during the surgical technique.

To lock the implant, the distal portion 108 of the main body 102 is uncovered by sliding the drive shaft 160 into the intermediate portion 154 of the hex nut driver 140. The drive shaft 160 is initially prevented from rotation because the pins 165 are riding in the slots 161 (best seen in FIG. 4). However, once the pins 165 bottom out in the slots 161, the user can hold the knob 148 and rotate the drive shaft 160 so the pins 165 come to rest in the radial portion 164 of the slots 161. As a result, the drive shaft 160 is retained in the intermediate portion 154 and will stay retracted even when released by the user.

A matching adapter 170 is slid over the distal portion 108 of the main body 102 so that the legs 175, 176 can be inserted into the square opening 158. Preferably, the locking tabs 177 provide an audible click when the legs 176 deflect outward into the transverse locking passage 157 to confirm positive engagement for the user. The user can also visually confirm proper positioning of the adapter 170 because the alignment ridge 178 should align with the indicator arrow 123 on the socket end 156 as shown in FIG. 19.

After positioning the adapter 170 on the drive shaft 160, the implant 200 can be partially engaged to the tip 113 by a snap friction fit. The tip 113 is slightly compressed, by virtue of the flexible arms 109, and passed into the proximal internal recess 250 of the implant 200 with the blades 220*a*, 220*b* of the implant 200 aligned with the flexible arms 109. The tip 113 stops within the recess 250 when the distal pushing end 112 sits within the transverse groove 253. At this point, the implant 200 is coupled to the insertion instrument 100 but not yet "locked."

Figure 10:
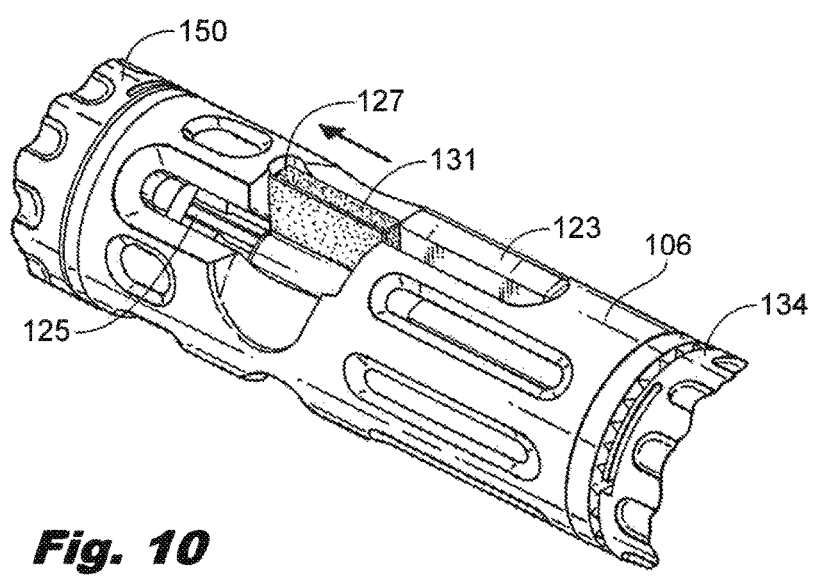
FIG. 10 is a perspective view of the handle of the insertion instrument of FIG. 1 with the plunger tab adjacent a transition wall.
Figure 11:
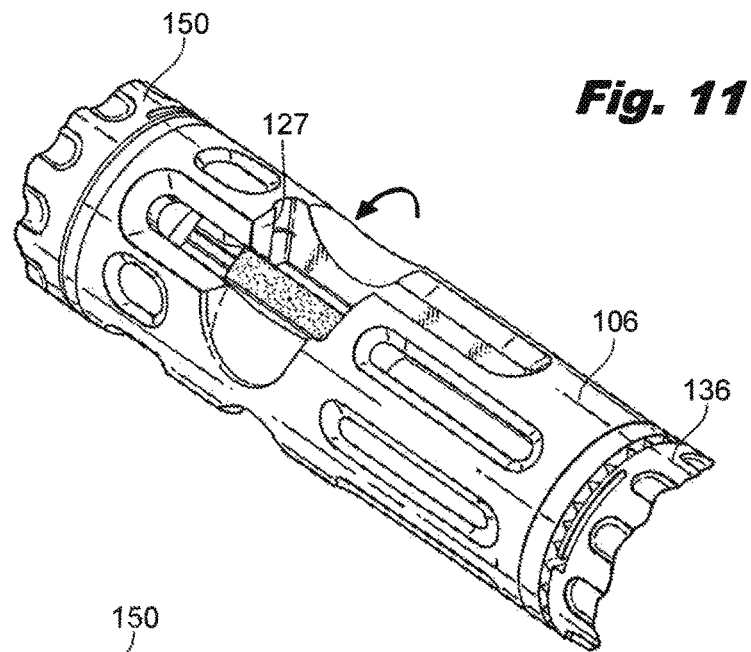
FIG. 11 is a perspective view of the handle of the insertion instrument of FIG. 1 with the plunger tab rotated.

To lock the implant 200 to the instrument 100, the plunger 110 is moved from the unlocked position to the locked position. To move the plunger 110 distally, the plunger knob 130 is rotated clockwise (looking from the proximal end) until the plunger tab 131 rests adjacent the transition wall 127, as shown in FIGS. 9 and 10. The distal pushing end 112 of the plunger 110 is approximately flush with the distal tip 113 of the main body 102. Thus, the flexible arms 109 of the main body 102 can no longer flex out of the transverse groove 253. Consequently, the implant 200 is tightly coupled and locked to the tip 113 so that inadvertent removal does not occur. The insertion instrument 100 is now ready to have the socket end 156 of the hex nut driver 140 engaged to the hex nut 235 of the implant 200.

To engage the hex nut driver 140 to the hex nut 235 of the implant 200, the handle portion 106 is held to prevent rotation while the drive shaft 160 is rotated to bring the pins 165 out of the radial portion 164 of the slots 161. The spring 163 will bias the drive shaft 160 outward so care should be taken to slowly extend the drive shaft 160 to have the hex socket 172 properly engage the hex nut 235 of the implant 200 (best seen in FIG. 22). In order to have the hex socket 172 properly engage the hex nut 235, a slight manual rotation or jiggle of the drive shaft 160 may be required. The implant 200 is now locked to the insertion instrument 100 to be ready for spinal implantation. The force provided by the spring 163 is optimized to insure proper, reliable engagement between the adapter 170 and hex nut 235 while providing excessive force to interfere with the operation of the insertion instrument 100 or deployment of the implant 200.

Deployment of the Implant in the Interspinous Space

FIGS. 20-23 illustrate various stages during insertion and placement of the implant into a target interspinous process space 382. Additional details are set forth in U.S. patent application Ser. No. 12/011,905, filed Jan. 30, 2008 (U.S. Pub. No. 2009/0054988), which is incorporated herein by reference in its entirety.

Figure 20:
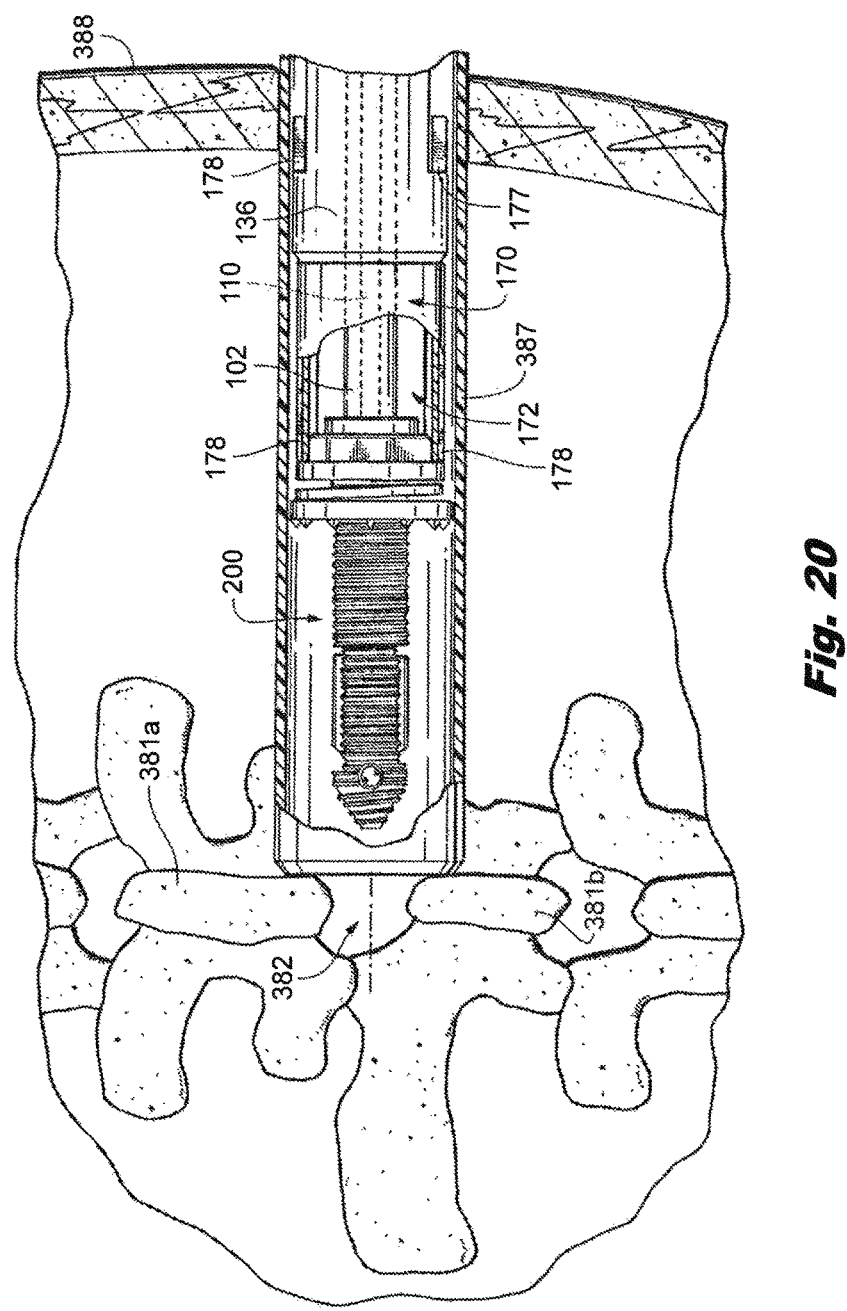
FIG. 20 is a dorsal view of an implant within an introducer tube during lateral insertion thereof.

FIG. 20 is a dorsal (rear) view of the implant 200, still held by the insertion instrument 100, within a lumen of an introducer tube 387, during lateral insertion thereof. For direct lateral insertion of the implant 200 into the target interspinous process space 382 an incision is formed in the skin 388 of a patient, and ultimately a sleeve 387 is advanced through the tissue to the target interspinous process space 382, through which the implant 200 is advanced, connected to the insertion instrument 100.

The implant 200 is axially rotated by way of the insertion instrument 100, thus threading the implant 200 into the target interspinous process space 382, distracting the adjacent spinous processes 381a, 381b, and advancing the implant 200, generally centered with respect to the spinous processes 381a, 381b.

Figure 21:
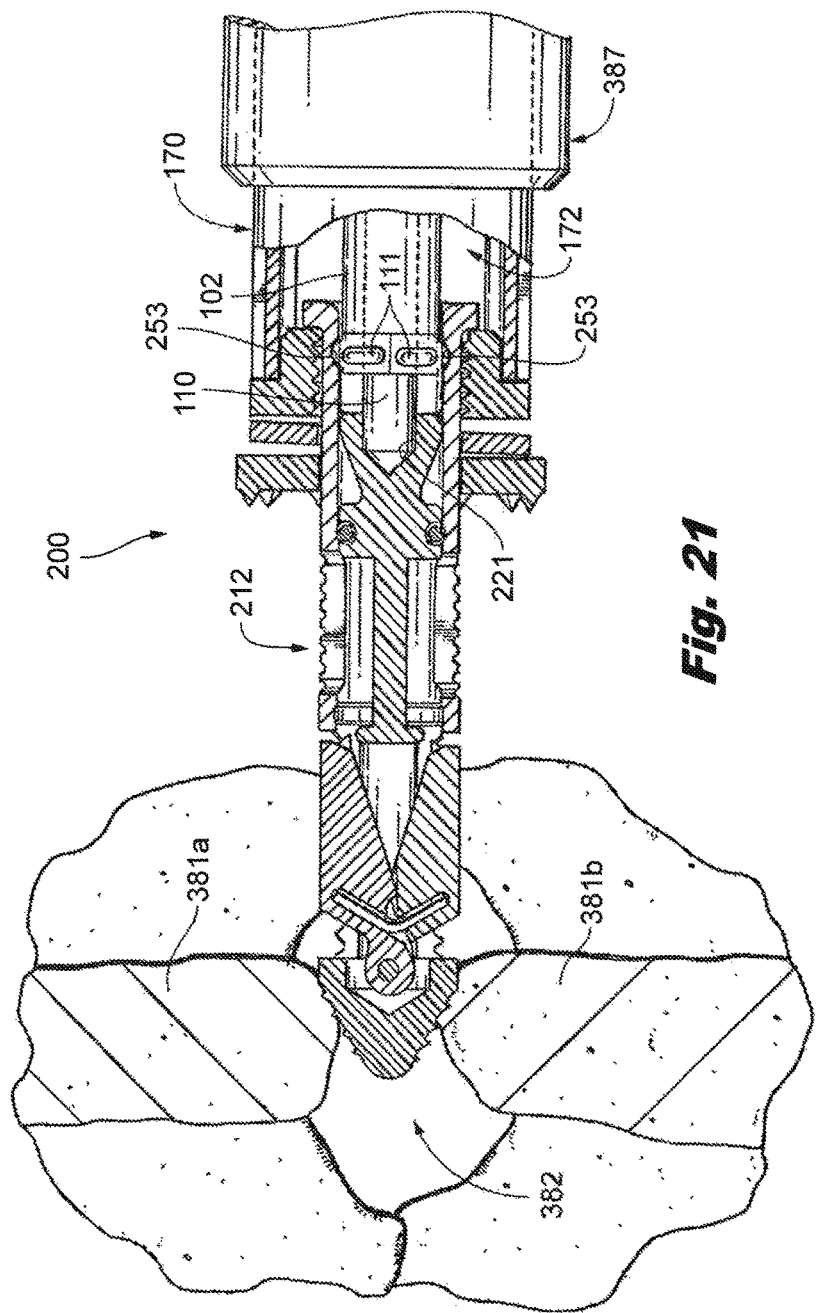
FIG. 21 is a dorsal view illustrating the implant being screwed into a target interspinous process space.

To rotate the implant 200, the proximal handle portion 103 of the main body 102 is rotated in a tightening or clockwise direction to self-thread the implant 200 through the interspinous space 382 as shown in FIG. 21. During the rotation of the implant 200, the implant 200 distracts the interspinous space. Relative rotation and axial translation between the implant 200 and the insertion instrument 100 is inhibited because the implant 200 is locked onto the tip 113 by the distal pushing end 112 of the plunger 110. Distraction can also be performed in advance by a separate instrument, with insertion of the implant 200 following, and maintaining such distraction.

Figure 22:
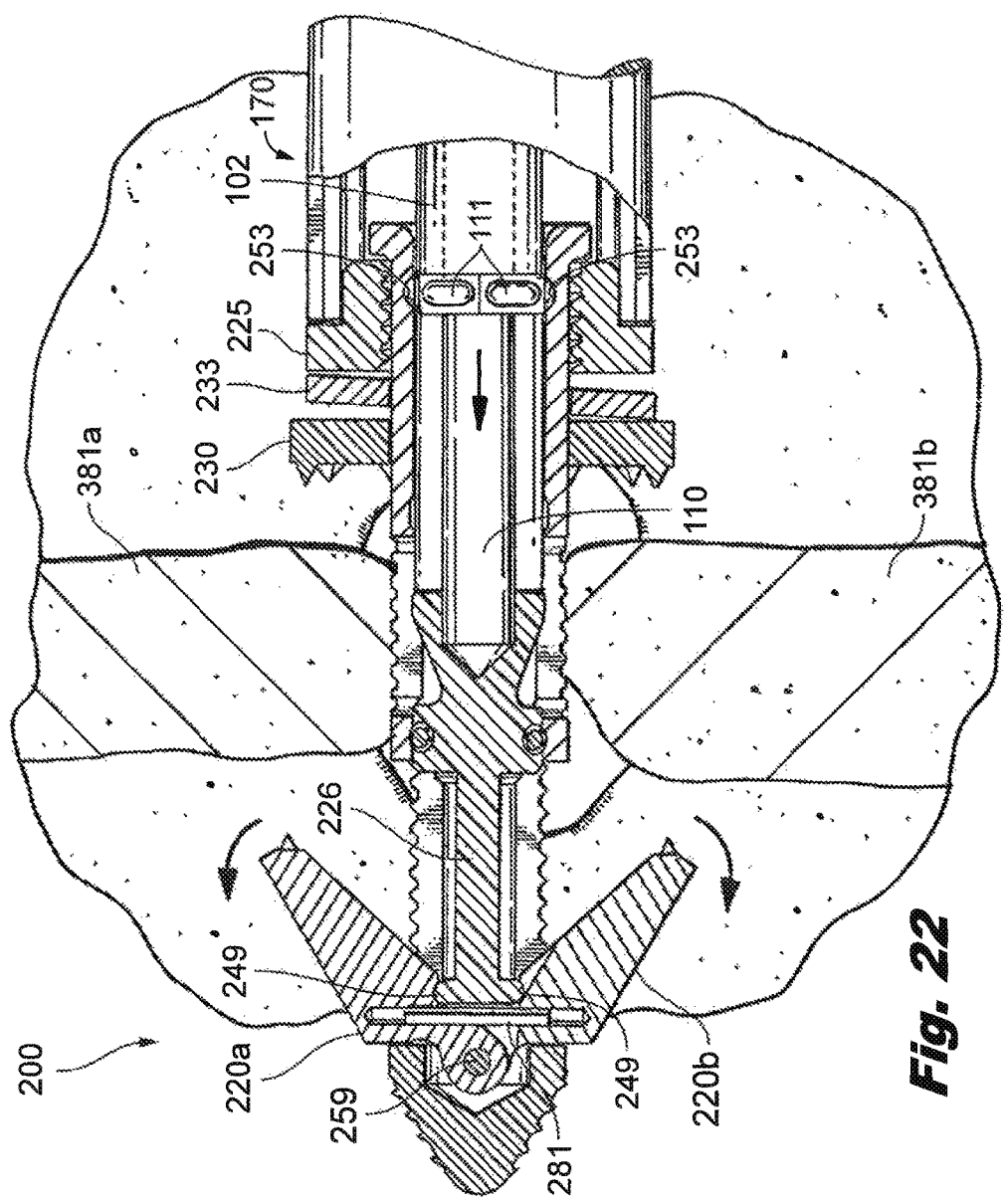
FIG. 22 is a cross-sectional view illustrating the deployment of the blades of the implant

When anchoring blades 220a, 220b have passed through the interspinous space 382 as shown in FIG. 22, the anchoring blades 220a, 220b can be deployed.

To deploy the implant 200, the handle 106 is rotated to translate the plunger tab 131 from the first path 123 to the second path 125 along the transition wall 127 (best shown in FIGS. 9-12). After the plunger tab 131 is fully positioned within the second path 125, the plunger knob 130 is again rotated clockwise to continue distal movement of the plunger tab 131.

Figure 12:
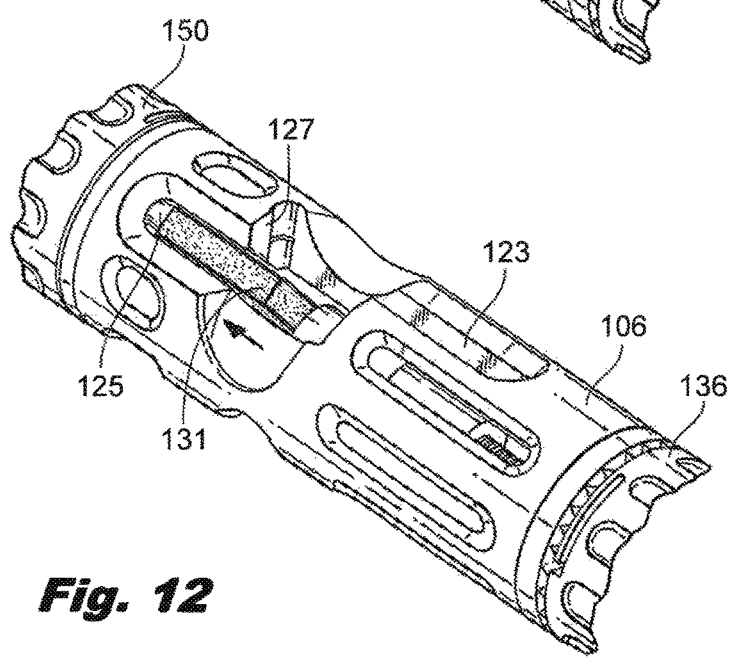
FIG. 12 is a perspective view of the handle of the insertion instrument of FIG. 1 with the plunger tab in a distal position.

As the plunger 110 continues to move distally, the distal pushing end 112 enters in the recess 221 of the implant plunger 226. As the plunger 110 continues to move distally, the distal pushing end 112 applies pressure and moves the implant plunger 226 distally to deploy the blades 220a, 220b. Once the plunger tab 131 is positioned in the distal most position of the staggered path 121 (as shown in FIG. 12), the implant is 'deployed'. The physician can also verify proper deployment of the blades 220a, 220b by fluoroscopy. Once the blades 220a, 220b are deployed, the implant 200 can be set in final position.

Figure 23:
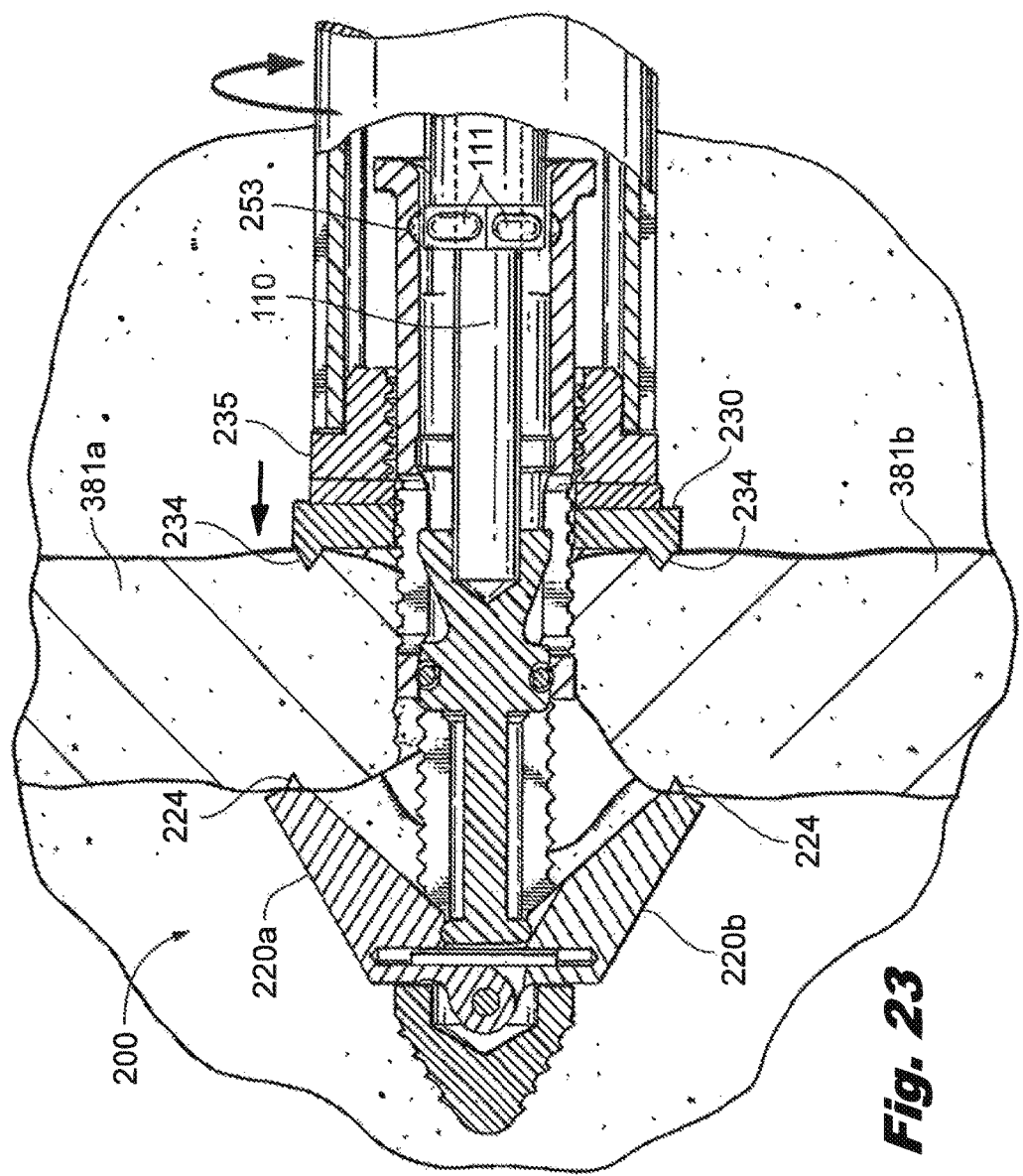
FIG. 23 is a cross-sectional view illustrating the hex nut driver securing the implant to the spinous process.

Referring now to FIG. 23, the hex nut 235 of the implant 200 is shown being driven by the hex nut driver 140 to engage the spikes 224, 234 to the spinous processes 381a, 381b. The hex nut driver 140 rotates the hex nut 235 to move the spike cap 230 distally. Because the spike cap 230 is keyed to the implant 200 to prevent rotation, as the hex nut 235 turns, the spike cap 230 slides distally.

To rotationally drive the hex nut 235, the knob 148 of the hex nut driver 140 is rotated clockwise relative to the main body 102. Turning the knob 148 turns the adapter 170 and thereby the hex nut 235. Once the spike cap 230 engages the spinous processes 381a, 381b, the blades 220a, 220b are drawn proximally into engagement with the bone 381a, 381b. A flat portion of the implant 200 is not threaded so that the implant 200 slides proximally. While the hex nut driver 140 is used to tighten the hex nut 235, the surgeon can feel the spike cap 230 become fully seated or full seating is seen in an accompanying fluoroscopy display.

Once the implant 200 is properly deployed, the insertion instrument 100 is disengaged from the implant 200. To disengage the insertion instrument 100, the drive shaft 160 of the hex nut driver 140 is retracted into the intermediate portion 154 with the pins 165 captured in the radial portion 164 of the slot 161 following the same procedure as described above so that the adapter 170 disengages from the hex nut 235.

To withdraw the plunger 110, the plunger knob 130 is loosened or rotated in the counter-clockwise direction relative to the handle portion 104 of the main body 102 to move the plunger tab 131 proximally. As the plunger tab 131 slides proximally within the staggered path 121, the distal pushing end 112 is translated distally.

Once the plunger tab 131 abuts the transition wall 127 the handle 106 is rotated so that the plunger tab 131 shifts from the second path 125 to the first path 123. The plunger knob 130 is loosened or rotated in the counter-clockwise direction relative to the handle portion 104 of the main body 109 to continue to slide the plunger tab 131 proximally. The plunger 110 is withdrawn from the tip 113 and the slots 109 are again allowed to flex so that the tip 113 pops out of the proximal internal recess 250 of the implant 200. With the adapter 170 disengaged and the plunger 110 retracted to the unlocked position, the coupling force of the tip 113 to the implant 200 can be overcome to fully detach the insertion instrument 100. Once removed, the insertion instrument 100 can be removed from the patient for disassembly, cleaning and re-use.

Disassembly of the Insertion Instrument

It is advantageous to disassemble the insertion instrument 100 for cleaning. Referring to FIGS. 3-10 in reverse, the plunger 110 can be removed from the main body 102. The plunger knob 130 can be unscrewed from the plunger 110. The main body 102 can be removed from the hex nut driver. The adapter 170 can be unsnapped from the hex nut driver 140. At this point, the components of the insertion instrument 100 are ready to be cleaned.

While the apparatuses and methods of subject invention have been shown and described with reference to preferred embodiments, it is to be understood that any feature described in connection with one embodiment can be advantageously applied to other embodiments of the invention, even if not explicitly described in connection therewith, if such feature(s) are not mutually exclusive with other features of such embodiment. Nevertheless, those skilled in the art will readily appreciate that further changes or modifications may be made to devices and methods of the present invention without departing from the spirit and scope thereof. It is also to be appreciated that the following claims can be rearranged, combined, combined with other features disclosed herein, presented in multiple dependent form and the like.

What is claimed is:

1. An insertion instrument for inserting an implant, the insertion instrument comprising:
   an elongated main body having a proximal handle and a distal portion that selectively couples to the implant;
   a plunger slidably engaged in a central passage of the elongated main body configured to fix the implant to the elongated main body by selectively filling the central passage within the distal portion; and
   a hex nut driver concentrically located about the plunger and elongated main body to deploy an actuation plunger of the implant,
   wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant,
   wherein the staggered path is a cut-out in the proximal handle that includes two parallel linear paths with a perpendicular transition wall therebetween.

2. The insertion instrument as recited in claim 1, further comprising a plunger knob rotatably coupled to the plunger wherein rotation of the knob translates the plunger tab within the staggered path.

3. The insertion instrument as recited in claim 1, wherein rotation of a plunger knob translates the plunger tab proximally and distally and wherein rotation of the handle transitions the plunger tab along the transition wall and between the two parallel linear paths.

4. The insertion instrument of claim 1, wherein the distal portion of the main body includes at least two flexible arms configured to friction fit the implant to the insertion instrument.

5. The insertion instrument of claim 1, wherein a tip of the distal portion of the main body matches an inner diameter of the implant thereby configured to control mounting, torqueing and retention of the implant with the main body.

6. An insertion instrument for inserting an implant, the insertion instrument comprising:
   an elongated main body having a proximal handle and a distal portion that selectively couples to the implant;
   a plunger slidably engaged in a central passage of the elongated main body configured to fix the implant to the elongated main body by selectively filling the central passage within the distal portion;
   a hex nut driver concentrically located about the plunger and elongated main body to deploy an actuation plunger of the implant,
   wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant; and
   a knob of the hex nut driver is rotatably coupled to a distal threaded portion of the handle through a distal end cap wherein the knob of the hex nut is configured to deploy the implant.

7. An insertion instrument for inserting an implant, the insertion instrument comprising:
   an elongated main body having a proximal handle and a distal portion that selectively couples to the implant;
   a plunger slidably engaged in a central passage of the elongated main body configured to fix the implant to the elongated main body by selectively filling the central passage within the distal portion;
   a hex nut driver concentrically located about the plunger and elongated main body to deploy an actuation plunger of the implant,
   wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant; and
   a plunger knob rotatably coupled to a proximal threaded portion of the handle through a proximal end cap wherein the plunger knob is configured to translate the plunger tab within the staggered path.

8. An insertion instrument for inserting an implant, the insertion instrument comprising:
   an elongated main body having a proximal handle and a distal portion that selectively couples to the implant;
   a plunger slidably engaged in a central passage of the elongated main body configured to fix the implant to the elongated main body by selectively filling the central passage within the distal portion;
   a hex nut driver concentrically located about the plunger and elongated main body to deploy an actuation plunger of the implant,
   wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant; and
   wherein the plunger tab, a plunger knob, and a knob of the hex nut driver include a black PVD coating configured to indicate portions of the insertion instrument that change position during operation.

9. An insertion instrument for inserting an implant, the insertion instrument comprising:
  an elongated main body having a proximal handle and a distal portion that selectively couples to the implant;
  a plunger slidably engaged in a central passage of the elongated main body configured to fix the implant to the elongated main body by selectively filling the central passage within the distal portion;
  a hex nut driver concentrically located about the plunger and elongated main body to deploy an actuation plunger of the implant,
  wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant; and
  a proximal end cap between a plunger knob and a proximal portion of the handle and a distal end cap between a distal portion of the handle and a knob of the hex nut driver.

10. The insertion instrument of claim 9, wherein the proximal end cap includes at least one flexible tooth corresponding to a plurality of ratchet teeth of the handle, the at least one flexible tooth and plurality of ratchet teeth configured to auto-lock the plunger and plunger knob to the handle and prevent premature loosening.

11. The insertion instrument of claim 9, wherein the distal end cap includes at least one flexible tooth corresponding to a plurality of ratchet teeth of the handle, the at least one flexible tooth and plurality of ratchet teeth configured to auto-lock the hex nut driver and the handle together and prevent premature loosening.

12. An insertion instrument for inserting an implant, the insertion instrument comprising:
  an elongated main body having a proximal handle and a distal portion that selectively couples to the implant;
  a plunger slidably engaged in a central passage of the elongated main body configured to fix the implant to the elongated main body by selectively filling the central passage within the distal portion;
  a hex nut driver concentrically located about the plunger and elongated main body to deploy an actuation plunger of the implant,
  wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant,
  wherein:
    in the unlocked position, the plunger tab is in the proximal most position of the staggered path;
    in the locked position, the plunger tab is positioned adjacent a transition wall of the staggered path; and
    in the deployed position, the plunger tab is in the distal most position of the staggered path.

13. An insertion instrument for inserting an implant, the insertion instrument comprising:
  an elongated main body having a proximal handle and a distal portion that selectively couples to the implant;
  a plunger slidably engaged in a central passage of the elongated main body configured to fix the implant to the elongated main body by selectively filling the central passage within the distal portion;
  a hex nut driver concentrically located about the plunger and elongated main body to deploy an actuation plunger of the implant,
  wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant,
  wherein the plunger tab is positioned at a proximal portion of the plunger and is generally rectangular with the plunger extending through a central portion thereof, and
  wherein the plunger tab includes at least two ball nose springs disposed on opposing faces of the plunger tab.

14. An insertion instrument for inserting an implant, the insertion instrument comprising:
  an elongated main body having a proximal handle and a distal portion that selectively couples to the implant;
  a plunger slidably engaged in a central passage of the elongated main body configured to fix the implant to the elongated main body by selectively filling the central passage within the distal portion;
  a hex nut driver concentrically located about the plunger and elongated main body to deploy an actuation plunger of the implant,
  wherein the proximal handle portion of the main body includes a staggered path therethrough for accepting a tab of the plunger therein and wherein advancement and retraction of the plunger tab within the staggered path alternates the insertion instrument between an unlocked position configured to mount the implant on the distal portion of the elongated main body, a locked position configured to lock the implant on the distal portion, and a deployed position configured to secure the implant,
  wherein the plunger tab is positioned at a proximal portion of the plunger and is generally rectangular with the plunger extending through a central portion thereof, and
  wherein the plunger tab includes flexible tabs disposed on opposing faces of the plunger tab.

15. An insertion device for a spinal implant, wherein the spinal implant includes:
  a) an elongated body to function as a spacer placed in a target interspinous process space between two adjacent spinous processes, wherein the body defines an interior and a proximal internal recess for access to the interior, the proximal internal recess forming a transverse groove;
  b) a distal anchor that is at least partially threaded and has opposing radially deployable blades mounted for rotation about a pin transversely mounted in the interior;
  c) a proximal anchor including a spike cap mounted to slide along the body and a drive nut mounted for longitudinal movement along the body between a first position spaced apart from the distal anchor and a second position relatively closer to the distal anchor to thereby compress the two adjacent spinous processes between the spike cap and the distal anchor; and d) an actuation plunger slidably inside the interior for moving the blades from a stowed position to an implant deployed position, the insertion device comprising:
   i) an elongated main body having a distal locking portion for coupling to the implant and a proximal handle portion, the main body defining a central passage and the distal locking portion having at least one flexible arm to flex radially inward;
   ii) a plunger slideably coupled in the central passage for movement between an unlocked position for mounting the implant on the distal locking portion, a locked position for locking the implant on the distal locking portion, and an insertion instrument deployed position for deploying the actuation plunger to move the blades from the stowed position to the deployed position;
   iii) a hex nut driver rotatably mounted on the main body having a socket end for engaging the drive nut to, in turn, move the hex nut, wherein the proximal handle portion of the main body includes a staggered path therethrough for accepting a tab of the plunger therein configured to control the advancement and retraction of the plunger within the central passage of the main body, wherein:
   in the unlocked position, when the implant is mounted on the insertion instrument, the plunger tab is in the proximal most position of the staggered path and the flexible arms are in the transverse groove;
   in the locked position, the plunger tab is positioned adjacent a transition wall of the staggered path, the flexible arms are in the transverse groove and the plunger extends through the central passage to be concentric with the flexible arms; and
   in the deployed position, the plunger tab is in the distal most position of the staggered path, the plunger extends out of the central passage to move the actuation plunger of the implant.

* * * * *